United States Patent
Celii et al.

(10) Patent No.: US 6,605,482 B2
(45) Date of Patent: Aug. 12, 2003

(54) PROCESS FOR MONITORING THE THICKNESS OF LAYERS IN A MICROELECTRONIC DEVICE

(75) Inventors: Francis G. Celii, Dallas, TX (US); Maureen A. Hanratty, Dallas, TX (US); Katherine E. Violette, Dallas, TX (US); Rick L. Wise, Plano, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 09/975,637

(22) Filed: Oct. 11, 2001

(65) Prior Publication Data

US 2002/0055197 A1 May 9, 2002

Related U.S. Application Data

(62) Division of application No. 09/711,125, filed on Nov. 9, 2000, now abandoned.

(51) Int. Cl.$^7$ ............................................... H01L 21/66
(52) U.S. Cl. ......................................................... 438/16
(58) Field of Search ........................... 438/5, 7, 14, 16, 438/478; 356/503, 504

(56) References Cited

U.S. PATENT DOCUMENTS 5,061,072 A * 10/1991 Folkard et al. .............. 356/369
5,337,150 A *  8/1994 Mumola ...................... 356/632
5,666,200 A *  9/1997 Drevillon et al. ........... 356/368
5,963,327 A * 10/1999 He et al. ..................... 356/369

OTHER PUBLICATIONS

Warnick et al., "Ellipsometry as a Sensor Technology for the Control of Deposition Processes", Decision and Control, Dec. 1998, Proceedings of the 37$^{th}$ IEEE Conference on, vol. 3, pp. 3162–3167.*

Jean–Louis et al., "SIMOX Layers and Interfaces Studies With A New Fast Multichannel Spectroscopic Ellipsometer", IEEE SOS/SOI Technology Conference, Oct. 1990, pp. 152–153.*

\* cited by examiner

*Primary Examiner*—Evan Pert
(74) *Attorney, Agent, or Firm*—Yingsheng Tung; Wade James Brady, III; Frederick J. Telecky, Jr.

(57) ABSTRACT

A method of determining the thickness of a thickness of a first layer of material in a semiconductor device using a reflectometer, the first layer of material being disposed outwardly from a second layer of material, the first and second layer of material both including silicon. The method includes generating at least one predicted behavior curve associated with a depth profile of an interface between the first and second layer of material, the predicted behavior curve including at least one expected optical measurement, the depth profile associated with the interface being present at a particular theoretical depth. The method also includes emitting light onto a surface of the semiconductor device. The method further includes collecting at least one optical measurement from portions of the emitted light that are reflected by the semiconductor device. The method additionally includes comparing the at least one optical measurement to the predicted behavior curve and determining the approximate actual depth of the interface in response to the compared optical measurement.

1 Claim, 4 Drawing Sheets

PROCESS FOR MONITORING THE THICKNESS OF LAYERS IN A MICROELECTRONIC DEVICE

This is a divisional application of application No. 09/711,125 filed Nov. 9, 2000, now abandoned.

TECHNICAL FIELD OF THE INVENTION

This invention relates in general to semiconductor processing, and more particularly to a process for monitoring the thickness of layers in a semiconductor device.

BACKGROUND OF THE INVENTION

Metrology of layers of semiconductor material that are formed of the same material of which the immediate underlying layer of semiconductor material is also formed is difficult because both layers display many of the same or similar physical properties. For example, no contrast between n-doped silicon or p-doped silicon and intrinsic silicon can be observed by scanning electron microscopy, which is one of the more common ways to determine layer thickness.

Present calibration methods utilized in such circumstances include destructive techniques such as profilometry, which uses a physical probe to measure a height differential, and transmission electron microscopy, which transmits electrons directly through wafers. Such methods may lead to wafer contamination, physical destruction of wafers, non-uniformity in testing, and/or excessive allocations of cost and time. Thus, optical techniques for determining semiconductor layer thickness are preferable alternatives. However, current optical techniques, such as fourier transform infrared spectroscopy (FTIR) using, for example, a BioRad instrument, or reflectometry using a ThermaWave instrument, for example, measure a thickness change in one semiconductor layer overlying a similar semiconductor layer.

For example, FTIR may seek to measure the thickness of an epitaxial silicon layer formed over a silicon substrate using optical detection of a change in dopant ion concentration. One problem with using FTIR to measure the thickness of particular layers of epitaxial silicon is that smaller thicknesses of silicon epitaxy are likely to be beneath the detection limit of the FTIR technique.

SUMMARY OF THE INVENTION

In accordance with the present invention, a process for monitoring the thickness of layers in a microelectronic device is provided that substantially eliminates or reduces disadvantages and problems associated with previous developed systems and methods.

In one embodiment of the present invention, a method is presented for determining the thickness of a thickness of a first layer of material in a semiconductor device using a reflectometer, the first layer of material being disposed outwardly from a second layer of material, the first and second layer of material both including silicon. The method includes generating at least one predicted behavior curve associated with a depth profile of an interface between the first and second layer of material, the predicted behavior curve including at least one expected optical measurement, the depth profile associated with the interface being present at a particular theoretical depth. The method also includes emitting light onto a surface of the semiconductor device. The method further includes collecting at least one optical measurement from portions of the emitted light that are reflected by the semiconductor device. The method additionally includes comparing the at least one optical measurement to the predicted behavior curve and determining the approximate actual depth of the interface in response to the compared optical measurement.

In another embodiment of the present invention, a method is presented for monitoring a thickness of a first layer of material in a semiconductor device using a reflectometer, the first layer of material being disposed outwardly from a second layer of material, the first and second layer of material both comprising silicon.

One advantage of the present invention is that it presents an improved process for monitoring the thickness of semiconductor layers that addresses disadvantages of present monitoring processes. An additional advantage of various embodiments of the present invention is that the thickness of a semiconductor layer of material may be achieved without destroying or contaminating wafers of semiconductor material. A further advantage of various embodiments of the present invention is that a process is presented for monitoring the thickness of material that can be performed on-line with semiconductor device manufacture. Yet another advantage of various embodiments of the present invention is that a process is presented for monitoring the thickness of semiconductor layers and material that allows the thickness of one semiconductor layer to be measured even when such semiconductor layer is formed on a second semiconductor layer having the same or a similar material composition.

BRIEF DESCRIPTION OF THE DRAWINGS

For a more complete understanding of the present invention and its advantages, reference is now made to the following description taken in conjunction with the accompanying drawings in which.

DETAILED DESCRIPTION OF THE INVENTION

Figure 1A:
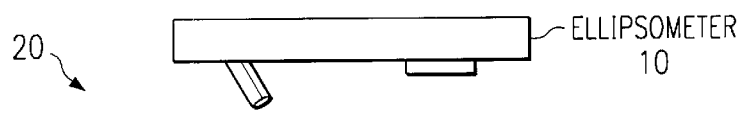
FIGS. 1A through 1C are schematic diagrams of a reflectometer and a cross-sectional view of a processing step in the creation of a semiconductor device illustrating one embodiment of the present invention.
Figure 1A:
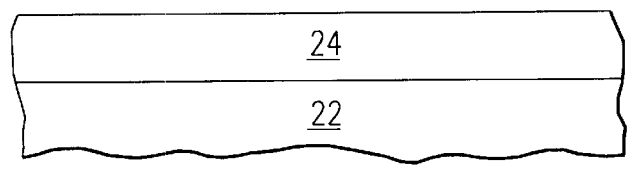
Figure 1B:
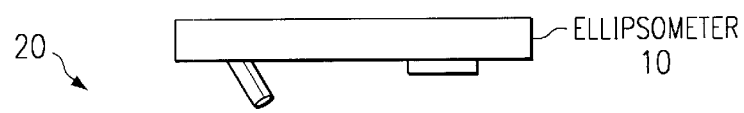
Figure 1B:
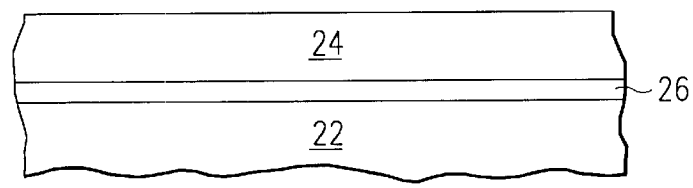
Figure 1C:
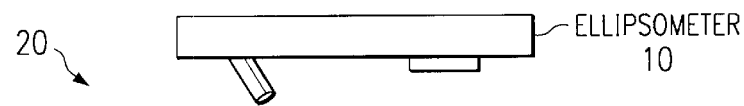
Figure 1C:
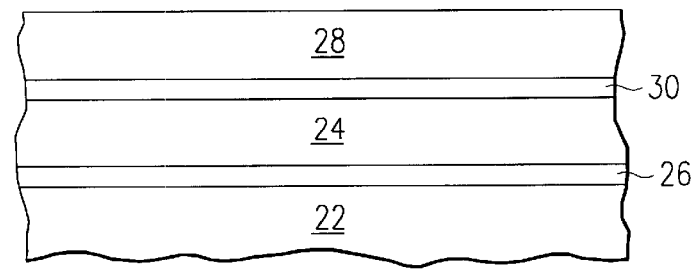

FIGS. 1A–C illustrate the use of a reflectometer such as ellipsometer 10 to monitor the thickness of layers of a semiconductor device 20. In particular, the reflectometer in the described embodiments of FIGS. 1A–1C is used to detect the thickness of a un-doped layer of material that is formed over a doped layer of material when both layers of material have the same or similar compositions.

In FIG. 1A, Semiconductor device 20 includes an un-doped substrate layer 22 and a doped substrate layer 24. Un-doped layer 22 is a monocrystalline silicon substrate. Doped layer 24 is an amorphous silicon layer amorphized because of damage to the crystalline structure of silicon caused by the implantation of either p- or n-type dopant ions. Un-doped layer 22 and doped layer 24 may have different optical characteristics, such as the magnitude of index of refraction, for example, because of such damage to the crystalline structure of doped layer 24. Similarly, optical characteristics between un-doped layer 22 and doped layer 24 may vary because of the introduction of the dopant ions into the silicon comprising doped layer 24. Although layers 22 and 24 are identified as being un-doped and doped layers of a silicon substrate, layers 22 and 24 may be any layers composed of the same or similar semiconductor material, such that the monitoring or detection of the thickness of doped layer 24 is desirable using ellipsometer 10.

FIG. 1A also illustrates ellipsometer 10 positioned over semiconductor device 20 such that light emitted by ellipsometer 10 may strike the surface of semiconductor device 20 and such that light reflected from semiconductor device 20 can be detected by ellipsometer 10. Ellipsometer 10 is a spectroscopic ellipsometer; however ellipsometer 10 may be any suitable ellipsometer or other reflectometer including an ellipsometer using one or more wavelengths of light. Many varieties of ellipsometer 10 are well known in the semiconductor processing industry, and may include any suitable number of light emission sources, wave guides, polarized or unpolarized lenses, light sensors, and processing components.

In operation, ellipsometer 10 directs beams of light at the surface of doped layer 24 at a suitable angle and intensity such that some photons from the beams of light are absorbed by semiconductor device 20 and some photons are reflected at different depths within semiconductor device 20 for detection by the detectors of ellipsometer 10. Ellipsometer 10 compares data perceived from the reflected photons in order to analyze differences at various depths of semiconductor device 20. In particular, ellipsometer 10 may examine the intensity and phases of light detected by ellipsometer 10 for each of one or more wavelengths of light.

Ellipsometer 10 may compare the intensity and phase data for a particular wavelength of light to known characteristics and models for: a given semiconductor material, a specific semiconductor material processed in a particular manner, or a specific interface known to form between two layers of the same semiconductor material after particular semiconductor processing techniques have been utilized. With regard to semiconductor device 20, models may be used that focus on changes in the optical properties of doped, amorphous silicon and un-doped, crystalline silicon. Ellipsometer 10 may compare data associated with the intensity and phase of light reflected by semiconductor device 20 to such models in order to determine the thickness of the amorphized silicon. A more detailed description of the operation of ellipsometer 10 and the modeling of such semiconductor material, processes, and interfaces is described more particularly with regard to the flow chart of FIG. 2.

FIG. 1B illustrates the anneal of doped layer 24. The amorphous silicon comprising doped layer 24 is annealed using a thermal anneal process. Such an anneal heals the crystalline lattice structure of the silicon. Importantly, the optical properties, such as the index of refraction and absorption coefficient, for example, of annealed doped layer 24 may closely resemble that of un-doped layer 22. However, the anneal of doped layer 24 generally does not result in the full anneal of doped layer 24 exactly at the interface between doped layer 24 and un-doped layer 22. Thus, a defect layer 26 of un-annealed doped layer 24 may remain between the annealed portion of doped layer 24 and un-doped layer 22. Alternatively, even if the anneal is relatively complete so as not to introduce optical changes caused by un-annealed silicon, the uneven interface between the crystalline structures of annealed doped layer 24 and un-doped layer 22 may provide a change in optical properties along such an interface. The presence of defect layer 26 and/or the uneven interface between layers 22 and 24 may be utilized by ellipsometer 10 to determine the thickness of annealed doped layer 24 using modeling of the optical properties of such defect layer 26 and/or such uneven interface. Such a determination may be made using the process described in reference to FIG. 2.

FIG. 1C illustrates the formation of a silicon epitaxial layer 28 outwardly from the annealed doped layer 24. Silicon epitaxial layer 28 may be formed using a suitable chemical vapor deposition process. For example, a chemical vapor deposition process may be used at a pressure of 40 torr, at a temperature of 850 degrees Celsius, and utilizing a flow rate of 24 slm $H_2$, 0.2 slm dichlorosilane, and 0.13 slm HCl. Formation of silicon epitaxial layer 28 may result in the formation of an interfacial layer 30 between the silicon epitaxial layer and the underlying doped layer 24. Even if interfacial layer 30 is not formed, differences in the index of refraction and absorption coefficient may result between un-doped silicon epitaxial layer 28 and doped layer 24. Either the presence of interfacial layer 30 and/or differences between doped and un-doped silicon may be used by ellipsometer 10 to determine the thickness of silicon epitaxial layer 28 using modeling of the optical properties of interfacial layer 30 and/or such differences between doped and un-doped silicon. Such a determination may be made using the process described in reference to FIG. 2.

Figure 2:
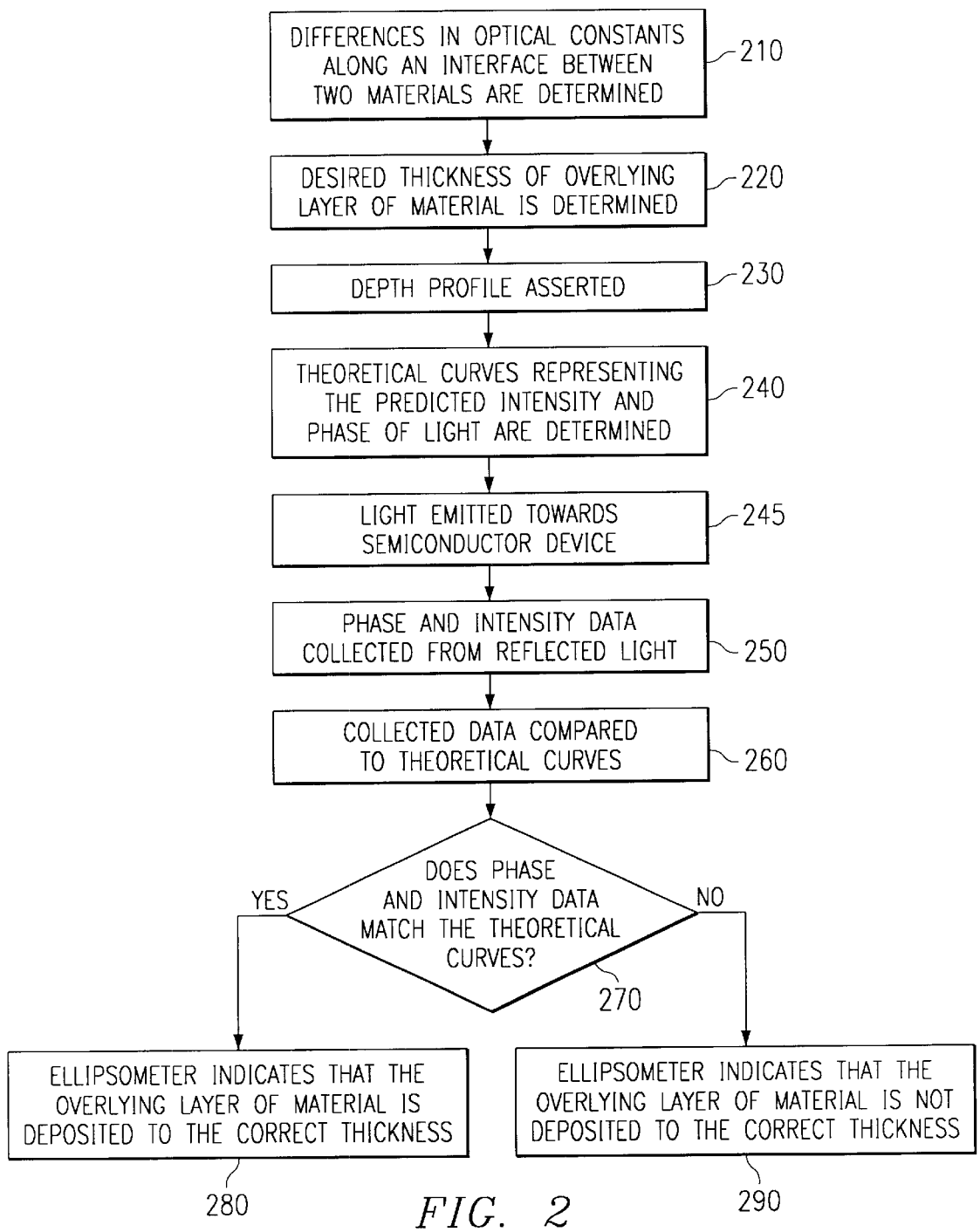
FIG. 2 is a flow chart illustrating the operation of the reflectometer to measure the thickness of materials according to another embodiment of the present invention.

FIG. 2 is a flow chart illustrating the operation of the ellipsometer 10 in order to measure the thickness of semiconductor material in semiconductor device 20.

In step 210, differences in the optical constants embodied by the refractive index 'n' and the absorption or extinction coefficient 'k' that are determined along interfaces between two different materials. Such differences may occur because of difference in material composition, roughness along an interface, the presence of dopants, gradients in material composition or dopant concentration, defects or damage to one or both of the layers such as end-of-range damage, the formation of defect or interfacial layers, and/or other differences brought about by the processing of the two materials (collectively referred to hereafter as "process factors"). Changes in 'n' and 'k' may be determined based on such process factors using relationships between the optical behavior of materials and standard ellipsometric equations. Such relationships and ellipsometric equations are described in general in the book "Optics," Volume 4, written by Arnold Summerfeld and published by the Academic Press in 1949.

In step 220, a desired thickness of an overlying layer of material to be formed on a semiconductor device is determined.

Figure 3A:
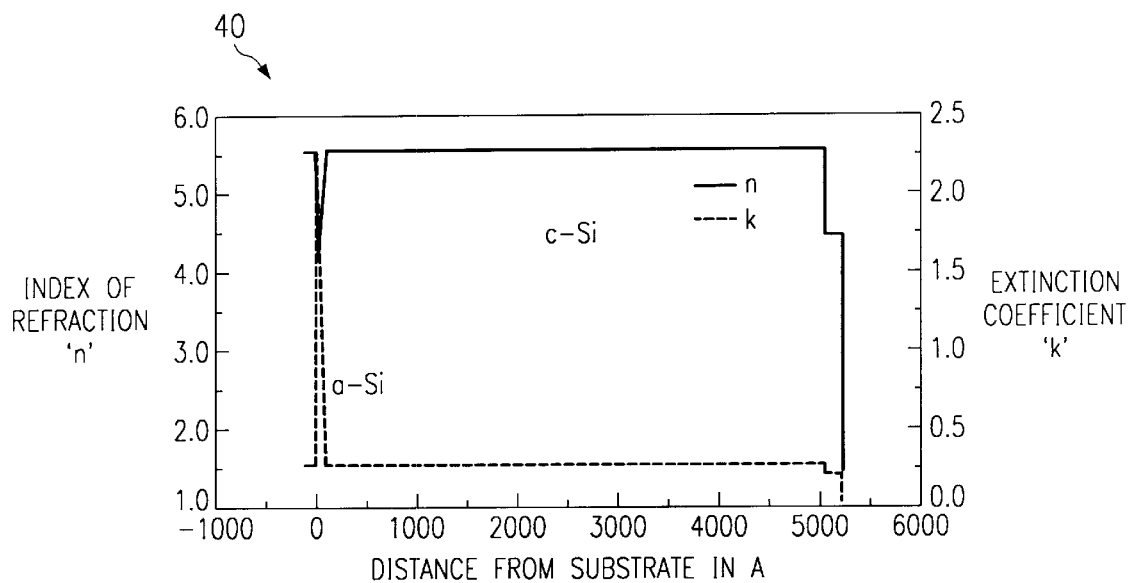
FIGS. 3A through 3C are diagrams representing the optical characteristics of a semiconductor device at a particular point in semiconductor processing.

In step 230, once changes in 'n' and 'k' are determined across an interface of two materials based on process factors in a given semiconductor process, and once the desired thickness of the overlying material is determined, such changes can be modeled and a depth profile 40 of optical constants may be asserted for use by ellipsometer 10. An example of depth profile 40 for a particular thickness of crystalline silicon over amorphous silicon is illustrated in FIG. 3A. The crystalline silicon over amorphous silicon profile 40 represents epitaxial layer 28 and partially-annealed doped layer 24 over defect layer 26 as described in reference to FIG. 1B.

In step 240, ellipsometer 10 may use depth profile 40 to construct predicted behavior curves 42 and 44 representing, respectively, the predicted intensity and phase of light reflected from semiconductor device 20 at various wavelengths of light and measured by ellipsometer 10. Such intensity and phase are conventionally represented by ellipsometer 10 as tangent(psi) and cosine(delta). Examples of both a predicted behavior tangent(psi) curve 42 and a predicted behavior cosine(delta) curve 44 are presented in FIGS. 3B and 3C that correspond to the predicted optical behavior of a device having an epitaxial silicon layer 28 deposited on a partially annealed layer of doped silicon 24. In the example illustrated by FIGS. 3B and 3C, doped silicon layer 24 is only partially annealed such that defect layer 26 is present. Thus, curves 42 and 44 may be generated by ellipsometer 10 based on the particular depth profile 40 illustrated in FIG. 3A.

Once ellipsometer 10 has generated curves 42 and 44 that are representative of the intensity and phase of light at various wavelengths, ellipsometer 10 may then utilize curves 42 and 44 during semiconductor processing in order to determine when or whether an overlying layer of material has reached the desired thickness. Thus, in step 245, beams of light are emitted by ellipsometer 10 to strike the surface of a semiconductor device. In step 250, ellipsometer 10 collects phase and intensity measurement data for different wavelengths of light that have been reflected from the semiconductor device during or after the formation of the overlying layer of material. In an alternative embodiment, data associated with only one wavelength of light may be utilized.

In step 260, ellipsometer 10 performs analytic techniques such as iterative processing and curve-fitting in order to attempt to match the collected phase and intensity data to curves during the formation of the overlying layer of material.

Figure 3B:
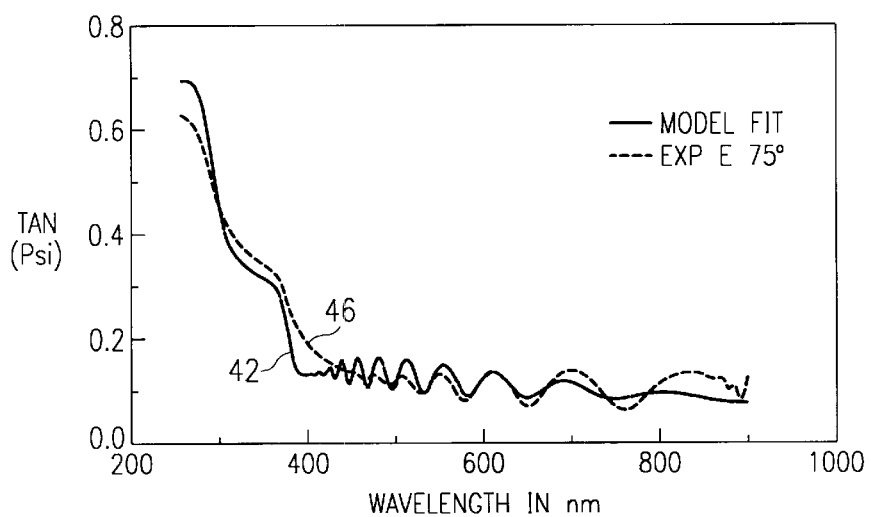
Figure 3C:
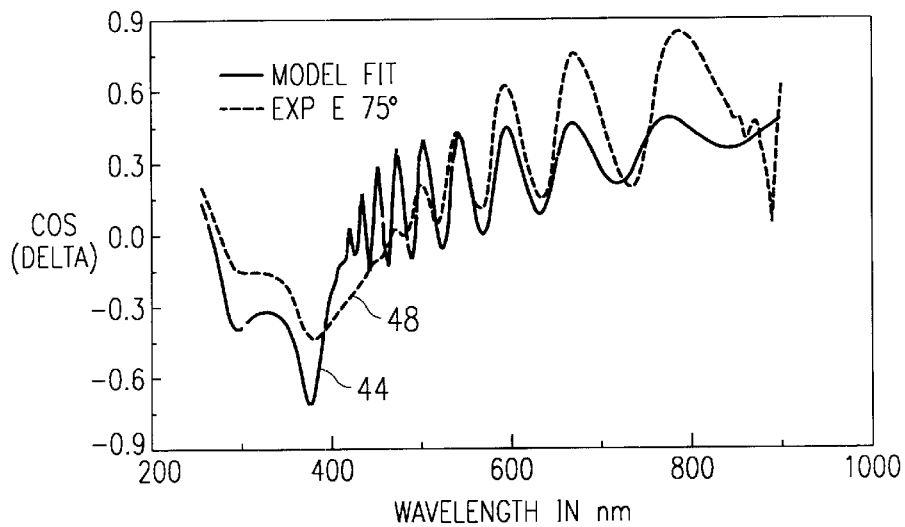

In step 270, ellipsometer 10 determines if the phase and intensity data closely match the optical data predicted by curves 42 and 44 as illustrated by the presence of dashed curves 46 and 48 in FIGS. 3B and 3C. If a match is identified, ellipsometer 10 indicates that the overlying layer of material is deposited to the correct thickness in step 280. If a match is not identified, ellipsometer 10 indicates that the overlying layer of material is deposited to an incorrect thickness in step 290.

Figure 4:
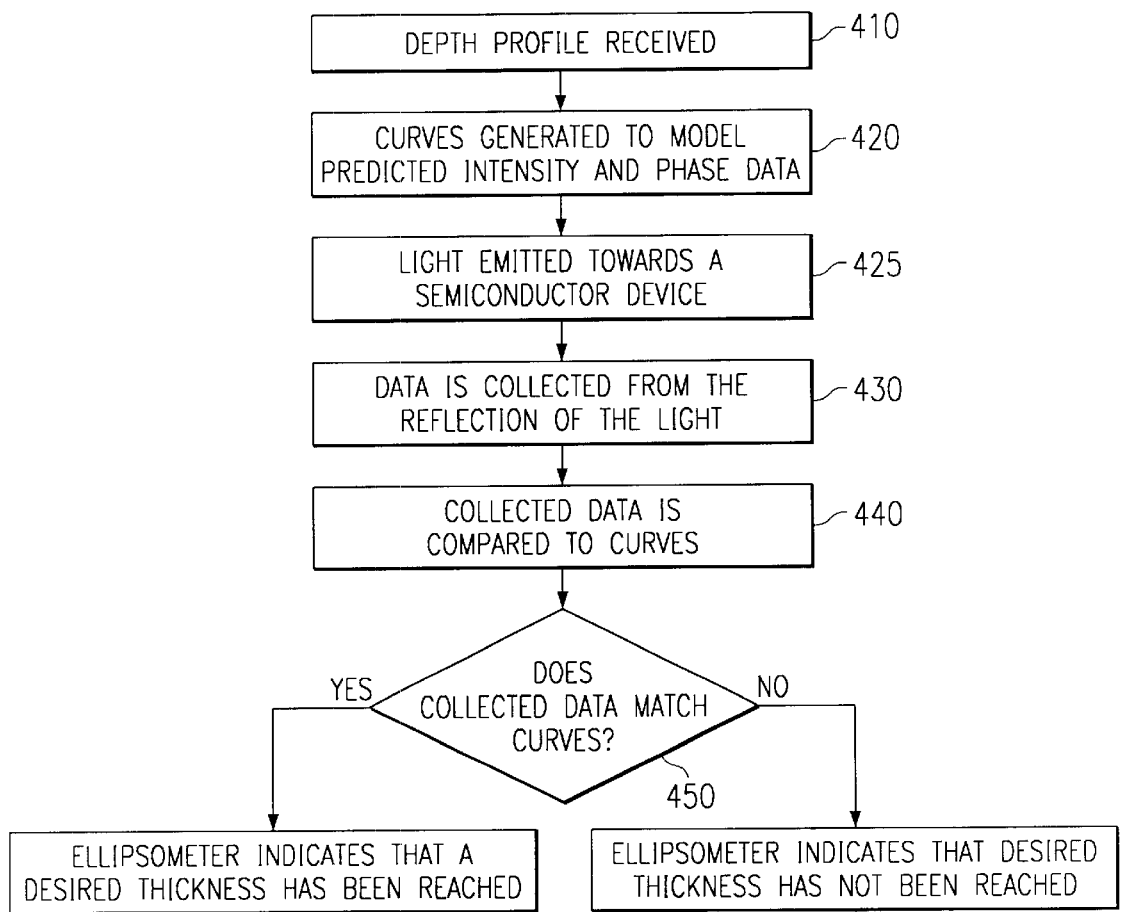
FIG. 4 is a flowchart of a particular embodiment of the operation illustrated in FIG. 2.

FIG. 4 illustrates a flowchart of a particular embodiment of the process illustrated in the flowchart of FIG. 2. More particularly, FIG. 4 illustrates a method for forming or verifying the formation of silicon epitaxial layer 28 to a desired thickness over a partially annealed doped layer 24 such that defect layer 26 is present.

In step 410, a particular depth profile 40 is received by ellipsometer 10, the particular depth profile corresponding to the optical behavior at defect layer 26 given a desired total thickness of partially annealed doped layer 24 and silicon epitaxial layer 28. In step 420, particular curves 42 and 44 are generated to model the intensity and phase of light reflected by semiconductor device 20 given the particular depth profile 40. In step 425, light generated by ellipsometer 10 is directed toward the surface of semiconductor device 20 during or after formation of silicon epitaxial layer 28. In step 430, data corresponding to the intensity and phase of light reflected by semiconductor device 20 in step 425 is collected. In step 440, the collected data is compared to the particular curves 42 and 44. In step 450, ellipsometer 10 determines if the collected data matches the particular curves 42 and 44. If there is a match, ellipsometer 10 indicates that a desired thickness has been reached in step 460. If there is no match between the collected data and curves 42 and 44, ellipsometer 10 indicates that the desired thickness has not been achieved in step 470.

In one embodiment, the processes described with reference to FIGS. 2 through 4 may be utilized to determine the thickness of a third layer of material using an interface between a first and second layer of material. For example, the thickness of an epitaxial layer of silicon may be determined by determining the thickness of an underlying annealed amorphous silicon layer before the formation of the epitaxial layer. In such an example, the thickness of the underlying annealed amorphous silicon may be determined by examining an interface between the annealed amorphous silicon and an underlying substrate.

Such an interface may have distinctive optical properties caused by, for example, the less than complete anneal of the annealed amorphous silicon. After the thickness of the underlying annealed amorphous silicon is determined, the same interface may again be examined after the formation of the epitaxial layer to determine a cumulative depth of the annealed amorphous silicon and epitaxial layer combined. By subtracting the depth of annealed amorphous silicon from the cumulative depth, the approximate depth of the epitaxial layer may be easily determined.

Although the present invention has been described using several embodiments, various changes and modifications may be suggested to one skilled in the art after a review of this description. It is intended that the present invention encompass such changes and modifications as fall within the scope of the appended claims.

What is claimed is:

1. A process for manufacturing a silicon integrated circuit product that includes a crystalline silicon substrate, a thin epitaxial silicon layer, and a thin silicon interface layer therebetween, comprising:

a. constructing a depth profile of a target structure including:
     i a silicon substrate having a certain thickness, a known index of refraction and extinction coefficient;
     ii a silicon interface layer overlaying the silicon substrate, having an empirical depth, index of refraction and extinction coefficient; and
     iii an epitaxial silicon layer overlaying the interface layer, having a desired thickness and the known index of refraction and extinction coefficient;

b. generating a first set of model behavior curves of the target structure, based on the depth profile, including:
     i an intensity change curve, also known as a tangent curve, also known as psi curve; and
     ii a phase change curve, also known as a cosine curve, also known as delta curve;

c. forming a thin silicon epitaxial layer having the known index of refraction and extinction coefficient over the product substrate, the forming also including the forming of some interface layer;

d. emitting light signals of certain wavelengths from an ellipsometer on the surface of the epitaxial layer at certain angles with respect to the surface of the epitaxial layer;

e. generating reflected light signals from the surface of the epitaxial layer and the interface layer;

f. collecting the reflected light signals with the ellipsometer;

g. generating a second set of behavior curves from the reflected light signals collected by the ellipsometer including:
   i an intensity change curve, also known as a tangent curve, also known as psi curve; and
   ii a phase change curve, also known as a cosine curve, also known as delta curve; and h. ascertaining the thickness of the formed epitaxial layer by comparing the first set and the second set of the behavior curves and calculating the difference, if any, between the target thickness and the formed thickness.

* * * * *